United States Patent [19]

Anstey

[11] Patent Number: 5,268,710
[45] Date of Patent: Dec. 7, 1993

[54] CHILDREN'S SUNGLASSES

[76] Inventor: Gail L. Anstey, 30 Whitney Pl., Buffalo, N.Y. 14201

[21] Appl. No.: 879,850

[22] Filed: May 6, 1992

Related U.S. Application Data

[63] Continuation-in-part of Ser. No. 705,148, May 24, 1991, abandoned.

[51] Int. Cl.$^5$ ............................................. G02C 5/14
[52] U.S. Cl. ................................... 351/121; 351/123; 351/156
[58] Field of Search .............. 351/156, 157, 123, 121, 351/41, 153, 44; 2/452, 450, 448

[56] References Cited

U.S. PATENT DOCUMENTS

| | | | |
|---|---|---|---|
| D. 175,269 | 8/1955 | Nelson | 351/41 |
| 2,660,092 | 11/1953 | Bloom | 351/156 |
| 4,779,291 | 10/1988 | Russell | 2/450 |

Primary Examiner—Bruce Y. Arnold
Assistant Examiner—Hung Xuan Dang
Attorney, Agent, or Firm—Darby & Darby

[57] ABSTRACT

Sunglasses for infants and small children are formed of a lens-defining member made of a thin flexible light-transmitting plastic material of a sun-protective composition or color. The lens-defining member has opposite projecting tabs to which flexible extendable strips are attached for supporting the sunglasses on the head of the wearer. A frame made of a soft flexible plastic foam material and having two superimposed frame members of substantially the same shape is formed by affixing each frame member to a respective face of the lens member.

6 Claims, 1 Drawing Sheet

CHILDREN'S SUNGLASSES

The present application is a continuation-in-part of my prior design patent application, Ser. No. 705,148, filed May 24, 1991 now abandoned.

BACKGROUND OF THE INVENTION

The present invention relates to sunglasses and, in particular, to children's sunglasses, such as for infants and small children.

There exists a large variety of sunglasses of different shapes and sizes and made of different materials. Some of the variety of sunglasses are designed for wearing by small children. The sunglasses to be worn by small children are usually made of a plastic frame with plastic lenses and having plastic side pieces, at opposite sides. However, despite the large variety of different sunglasses, such sunglasses are not suitable for very small children or infants, as the frames and other parts are relatively rigid and subject to breaking, which products have relatively sharp edges that can injure an infant or small child, or small parts which may break free causing injury.

SUMMARY OF THE INVENTION

An object of the invention is to provide sunglasses that can be worn by infants and small children without danger of being injured by them.

Another object of the invention is to provide children's sunglasses that can be manufactured easily and at low cost.

These and other objects of the invention, which will become apparent below, are achieved by providing sunglasses having a lens-defining strip and a band formed as a unit, and having two superimposed inner and outer non-stress bearing frame members of substantially the same shape made of a soft flexible plastic material. The lens-defining means is preferably made of a thin flexible light-transmitting material of a sun-protective material or color and secured between the two frame members, preferably by cementing. The lens-defining means preferably comprises a single lens-defining member and may have opposite tabs projecting beyond the lateral edges of the frame and to which flexible strips are attached to provide a band for supporting the sunglasses on the head of the wearer. The inner and outer frame members may, for example, be made of polyurethane-type foam materials and the lens-defining member may be made of a thermosetting flexible plastic sheet material. The band is made as two tubular members, preferably of a soft, adjustable-length (e.g., crinkled) textile material. Each band member is attached at one end to one of the projecting tabs of the lens member, which tab is received within the corresponding tubular member, and has, at the other free end thereof, one mating part of Velcro TM means or other fastener for adjustably attaching the free ends to each other when the sunglasses are put on the wearer's head. The bands may be attached to the tabs by stitching, gluing, stapling or the like.

The present invention will be best understood from the following detailed description of the preferred embodiment when read with reference to the accompanying drawings.

DETAILED DESCRIPTION OF A PREFERRED EMBODIMENT

Figure 1:
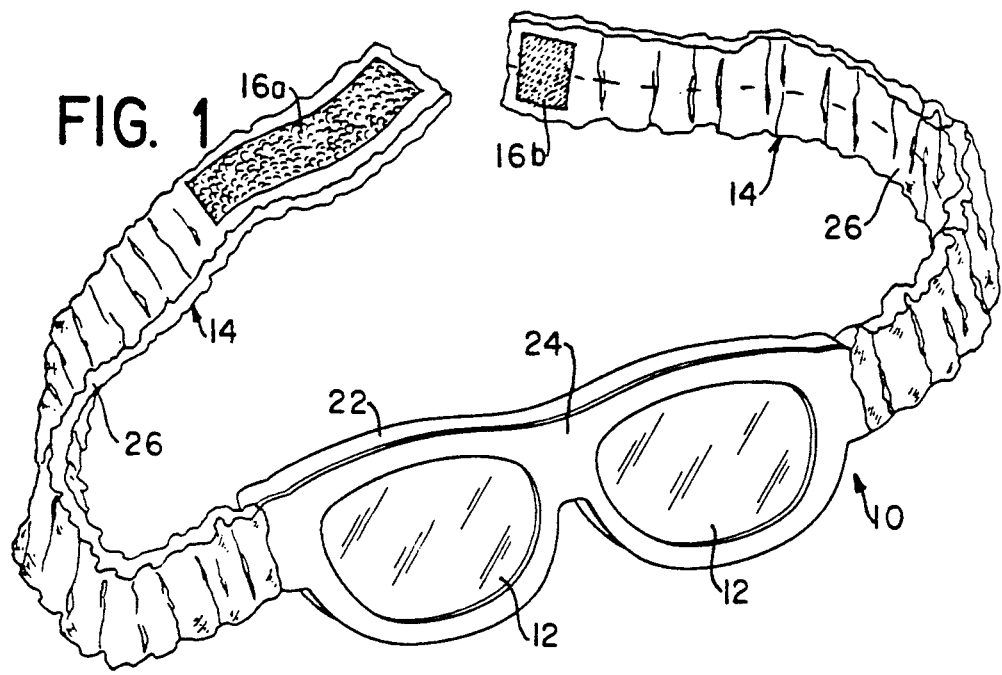
FIG. 1 shows a perspective view of sunglasses according to the present invention.

As shown in FIG. 1, the sunglasses according to the present invention have a frame 10, a lens-defining member 12 and two strips 14, each secured at one end thereof at a respective lateral side of the frame and together forming a head band. At their free ends, the strips 14 have Velcro TM parts 16a and 16b for adjustably connecting the strips at their free ends. As can be seen in FIG. 1, the two Velcro TM parts may have different lengths. This permits accommodating different sizes of heads of different wearers and more economical use of Velcro TM material. As shown, the Velcro TM parts 16a and 16b are attached to respective free ends of the strip 14 by stitching, but may, of course, be secured by any other appropriate means, e.g., cementing or stapling. Other suitable fastening means may be used in place of the Velcro TM parts, such as snaps, ties, buttons or buckles.

Figure 2:
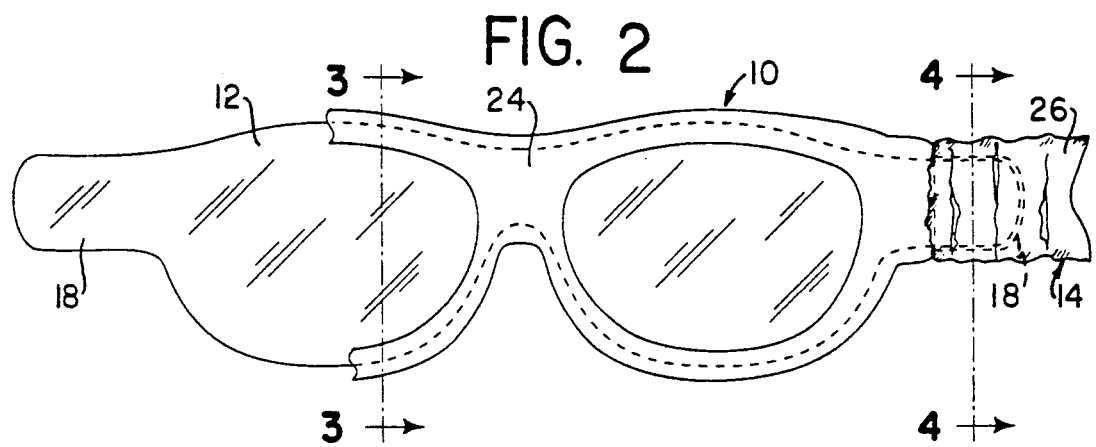
FIG. 2 shows a partial front elevational view of sunglasses according to the present invention with one band portion removed.
Figure 3:
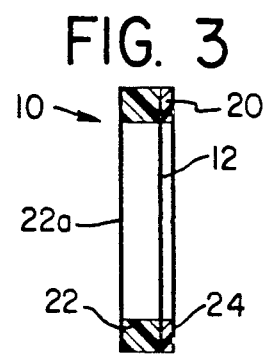
FIG. 3 shows a cross-sectional view along lines 3—3 in FIG. 2.
Figure 4:
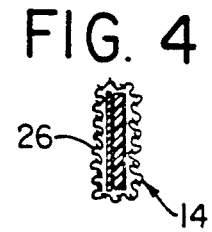
FIG. 4 shows a cross-sectional view along lines 4—4 in FIG. 2.

The lens-defining member 12 is a single piece made of a thin plastic light-transmitting material of a sun-protective composition or color, preferably a thermosetting material. A preferred material is high-performance Lexan TM film, which has the desirable properties of providing ultraviolet protection, being shatter and chemical resistant and lightweight and flexible. Where desired, other materials may be used, including materials suitable for forming optical lenses or curvatures prescribed for the individual wearer. The lens-defining member 12 has, at opposite ends thereof, respective tabs 18 which project beyond respective lateral edges of the frame 12 and to which respective strips 14 (only one is shown in FIG. 2) are secured. The lens-defining member 12 is positioned, as shown in FIG. 3, between an outer frame member 20 and an inner frame member 22, which are preferably held to the lens member by gluing. A single-piece lens-defining member is preferably used, with a tab member at each side edge. A third frame member layer 24 may be glued onto the outer surface of the frame member 20 for decorative purposes. The inner frame member 22 may also be provided with an inner (face) layer 22a of material similar to the outer layer 24.

The outer and inner frame members 20 and 22 may be made of polyurethane-type foam materials, of the same or different porosity. A preferable material is polyethylene foam (e.g., Voltek brand) which is lightweight, flexible, without sharp edges and printable or embossable for decoration purposes.

The band strips 14 are generally formed as tubular members 26 or with tubular ends, generally of a soft flexible textile material with a means to permit adjustment in length. The strips 14 are secured to tabs 18 which are received within the tubular ends of the strips 14 which, therefore, cover and protect the wearer from possible injury from the tabs. The strips 14 are secured to tabs 18 preferably by stitching. However, other securing means, i.e., glue or staples, may also be used. The flexible band provides adjustability to accommodate different sizes and usual growth of children's head size and insures firm seating of the sunglasses on the wearer's head, while the soft material provides for comfortable feeling.

The materials of the frame members and band strips are soft and flexible, and isolate the lens members from contact the wearer, for enhanced comfort in wearing. The materials of the frame members and band strips lend themselves readily to printing or outer coloring for decorative purposes. The strips may have on their opposite surfaces different color drawings, letters, numbers, etc. for decoration purposes and to make them more attractive to children.

Thus, the frame members not only may serve a cosmetic function, but also serve to space the lens-defining member from the wearer's eyes, and protect the lens from scratching or other damage when the eyeglasses are laid down. Contrary to conventional eyeglasses, the frame is not a structural element; the structure is provided by the unitary construction of the lens-defining member and the band strips, without depending upon the frame members.

As can be seen from the foregoing description, the present invention provides sunglasses which an infant or small child can wear without any danger of injury. Because of softness and flexibility of the frame and softness of the holding strips, the sunglasses, according to the invention, are very comfortable to wear and absence of likelihood of breakage or sharp edges or small parts breaking free prevents injury to an infant or small child wearing the sunglasses. The preferred materials are hand-washable, permitting continued use despite possible soiling.

Further, as follows from the foregoing description, the sunglasses of the present invention can be manufactured in a simple way from low-cost and even leftover or scrap materials. Therefore, their cost is small.

While a particular embodiment of the invention has been shown and described, various modifications thereof will be apparent for those skilled in the art and, therefore, it is not intended that the invention be limited to the disclosed embodiment or to the details thereof, and departures may be made therefrom within the spirit and scope of the invention as defined in the appended claims.

What is claimed is:

1. Sunglasses for infants or small children comprising lens-defining means made of a flexible thin sun-protective light-transmitting material; the lens-defining means having an attachment tab extending laterally from each side; a band formed of two flexible soft strips each attached to one of said attachment tabs, respectively, and forming a unitary construction with said lens-defining member, for supporting the sunglasses on the head of the wearer; and a frame made of soft flexible material and having superimposed inner and outer frame members of substantially the same shape; said frame members being positioned on either face of said lens means;
the outer and inner frame members being made of a foam material, and said lens-defining member being made of a thermosetting plastic material, and each of said strips comprising a tubular member;
said lens-defining means comprising a single lens-defining member, and said attachment tabs forming diametrally opposite parts of said lens-defining member and projecting beyond respective lateral edges of said frame members.

2. Sunglasses for infants or small children comprising lens-defining means made of a flexible thin sun-protective light-transmitting material; the lens-defining means having an attachment tab extending laterally from each side; a band formed of two flexible soft strips each attached to one of said attachment tabs, respectively, and forming a unitary construction with said lens-defining member, for supporting the sunglasses on the head of the wearer; a frame made of soft flexible material and having superimposed inner and outer frame members of substantially the same shape; said frame members being positioned on either face of said lens means;
said lens-defining means comprising a single lens-defining member, said attachment tabs forming diametrally opposite parts of said lens-defining member and projecting beyond respective lateral edges of said frame members;
the outer and inner frame members being made of a foam material, said lens-defining member being made of a thermosetting plastic material, each of said strips comprising a tubular region; and
each strip being attached to a respective attachment tab with said tab being located within a respective tubular member.

3. Sunglasses for infants or small children comprising lens-defining means made of a flexible thin sun-protective light-transmitting material; the lens-defining means having an attachment tab extending laterally from each side; a band formed of two flexible soft strips each attached to one of said attachment tabs, respectively, and forming a unitary construction with said lens-defining member, for supporting the sunglasses on the head of the wearer; and a frame made of soft flexible material and having superimposed inner and outer frame members of substantially the same shape; said frame members being positioned on either face of said lens means;
said frame including a third flexible frame member having substantially the same shape as said first and second members, attached to the outer surface of said frame, said inner frame member being made of the same material as said outer frame member.

4. The method of fabricating sunglasses or the like suitable for infants and small children including the steps of:
providing a lens-defining means having an attachment tab extending from each of the opposite edges thereof;
affixing to each attachment tab a soft flexible band portion having a tubular portion at one end surrounding a respective tab;
providing on the other ends of said band portions means for adjustably holding said band portions together; and
affixing to said lens-defining member at least one frame member of a soft flexible and compressible material.

5. The method as in claim 4, wherein said lens-defining means is a single sheet of light-transmitting material blocking undesired light components.

6. The method as in claim 5, comprising affixing a frame member to each of the two faces of said lens-defining sheet.

* * * * *